(12) United States Patent
Boutoussov

(10) Patent No.: US 7,303,397 B2
(45) Date of Patent: Dec. 4, 2007

(54) CARIES DETECTION USING TIMING DIFFERENTIALS BETWEEN EXCITATION AND RETURN PULSES

(75) Inventor: Dmitri Boutoussov, Dana Point, CA (US)

(73) Assignee: Biolase Technology, Inc., Irvine, CA (US)

( * ) Notice: Subject to any disclaimer, the term of this patent is extended or adjusted under 35 U.S.C. 154(b) by 260 days.

(21) Appl. No.: 11/203,399

(22) Filed: Aug. 12, 2005

(65) Prior Publication Data

US 2006/0099548 A1 May 11, 2006

Related U.S. Application Data

(60) Provisional application No. 60/601,437, filed on Aug. 13, 2004.

(51) Int. Cl.
*A61C 3/00* (2006.01)
(52) U.S. Cl. ......................................... 433/215; 433/29
(58) Field of Classification Search ................. 433/215
See application file for complete search history.

(56) References Cited

U.S. PATENT DOCUMENTS

| | | | |
|---|---|---|---|
| 4,445,892 A | 5/1984 | Hussein et al. |
| 4,718,417 A | 1/1988 | Kittrell et al. |
| 4,913,142 A | 4/1990 | Kittrell et al. |
| 4,931,047 A | 6/1990 | Broadwin et al. |
| 4,985,027 A | 1/1991 | Dressel |
| 5,102,410 A | 4/1992 | Dressel |
| 5,196,004 A | 3/1993 | Sinofsky |
| 5,263,950 A | 11/1993 | L'Esperance, Jr. |
| 5,741,247 A | 4/1998 | Rizoiu et al. |
| 5,785,521 A | 7/1998 | Rizoiu et al. |
| 5,825,958 A | 10/1998 | Gollihar et al. |
| 6,106,516 A | 8/2000 | Massengill |
| 6,118,521 A | 9/2000 | Jung et al. |
| 6,254,597 B1 | 7/2001 | Rizoiu et al. |
| 6,334,069 B1 | 12/2001 | George et al. |
| 6,389,193 B1 | 5/2002 | Kimmel et al. |
| 6,669,685 B1 | 12/2003 | Rizoiu et al. |
| 2006/0142745 A1 | 6/2006 | Boutousov |

FOREIGN PATENT DOCUMENTS

| | | |
|---|---|---|
| JP | 2003001465 | 1/2003 |
| WO | 97 07928 | 3/1997 |

OTHER PUBLICATIONS

International Search Report, Sep. 25, 2006, PCT/US05/28909.
Written Opinion, Sep. 25, 2006, PCT/US05/28909.
International Search Report, Oct. 5, 2006, PCT/US05/28095.
Written Opinion, Oct. 5, 2006, PCT/US05/28095.

*Primary Examiner*—Cris Rodriguez
*Assistant Examiner*—Candice C Stokes
(74) *Attorney, Agent, or Firm*—Stout, Uxa, Buyan & Mullins, LLP

(57) ABSTRACT

A laser device is disclosed that directs light to a tooth and analyzes scattered light reflected from the tooth. The device measures a time delay between excitation and reflections of light. Reflected light is analyzed to determine a presence and extent of dental caries on the tooth.

16 Claims, 7 Drawing Sheets

CARIES DETECTION USING TIMING DIFFERENTIALS BETWEEN EXCITATION AND RETURN PULSES

CROSS-REFERENCE TO RELATED APPLICATIONS

This application claims the benefit of U.S. Provisional Application No. 60/601,437, filed Aug. 13, 2004 and entitled CARIES DETECTION USING TIMING DIFFERENTIALS BETWEEN EXCITATION AND RETURN PULSES, the entire contents of which are incorporated herein by reference. This invention relates to U.S. application Ser. No. 11/186,619, filed Jul. 20, 2005 and entitled CONTRA-ANGLE ROTATING HANDPIECE HAVING TACTILE-FEEDBACK TIP FERRULE, and to U.S. application Ser. No. 11/203,677, filed Aug. 12, 2005 and entitled LASER HANDPIECE ARCHITECTURE AND METHODS, the entire contents of both which are incorporated by reference herein.

BACKGROUND OF THE INVENTION

1. Field of the Invention

The present invention relates generally to electromagnetic energy procedural devices and, more particularly, to the use of electromagnetic energy device used in dental applications.

2. Description of Related Art

Early detection of dental caries is one important method for promoting dental health. While traditional methods of dental caries detection relied upon visual observation by a dental practitioner, other techniques have been developed that may be capable of augmenting the ability of a dental professional to detect dental caries. At least one of these methods, described more fully in U.S. Pat. No. 5,306,144, entitled DEVICE FOR DETECTING DENTAL CARIES, the entire contents of which are incorporated herein by reference, involves use of a laser that directs monochromatic light onto a tooth. Carious areas of the tooth are known to respond to the light by issuing fluorescent radiation that is characteristic of caries and that differs in intensity and spectral distribution from radiation returned from a healthy tooth. Reflected radiation may, therefore, be used to detect dental caries. A need exists in the prior art to improve the sensitivity and information content of dental caries detection.

SUMMARY OF THE INVENTION

The present invention addresses this need by providing a method of detecting dental caries comprising directing excitation pulses of laser energy toward a surface of a tooth and receiving corresponding return pulses of fluorescent radiation responsive to the laser energy. According to an implementation of the method, a time delay between the excitation pulses and the return pulses is determined.

An embodiment of the present invention can include an apparatus for detecting dental caries comprising a laser device capable of generating excitation pulses of laser energy, a delivery system capable of directing the excitation pulses toward a surface of a tooth, and a detector capable of receiving return pulses of fluorescent radiation according to the excitation pulses. The apparatus further can include a controller capable of measuring a time delay between transmission of excitation pulses and reception of corresponding return pulses.

While the apparatus and method has or will be described for the sake of grammatical fluidity with functional explanations, it is to be expressly understood that the claims, unless expressly formulated under 35 U.S.C. 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. 112 are to be accorded full statutory equivalents under 35 U.S.C. 112.

Any feature or combination of features described herein are included within the scope of the present invention provided that the features included in any such combination are not mutually inconsistent as will be apparent from the context, this specification, and the knowledge of one skilled in the art. For purposes of summarizing the present invention, certain aspects, advantages and novel features of the present invention are described herein. Of course, it is to be understood that not necessarily all such aspects, advantages or features will be embodied in any particular embodiment of the present invention. Additional advantages and aspects of the present invention are apparent in the following detailed description and claims that follow.

DETAILED DESCRIPTION OF THE INVENTION

Figure 1:
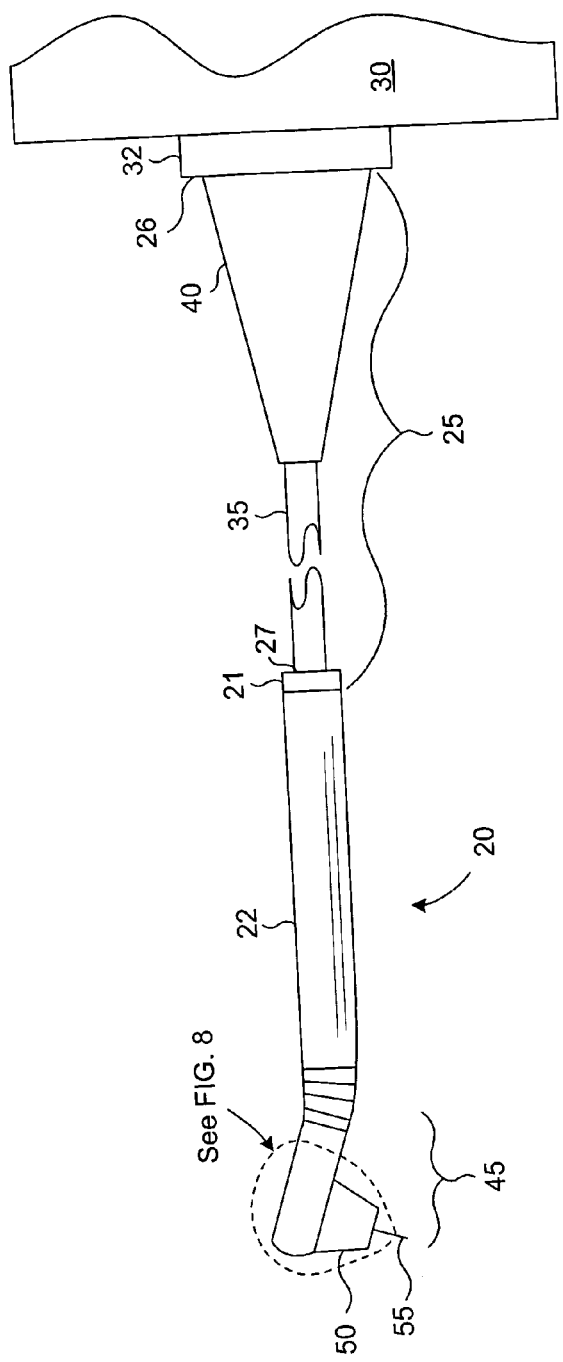
FIG. 1 is a pictorial diagram of a delivery system capable of transferring electromagnetic energy to a treatment site in accordance with an example of the present invention.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims. It is to be understood and appreciated that the process steps and structures described herein do not cover a complete process flow for operation of laser devices. The present invention may be practiced in conjunction with various techniques that are conventionally used in the art, and only so much of the commonly practiced process steps are included herein as are necessary to provide an understanding of the present invention. The present invention has applicability in the field of laser devices in general. For illustrative purposes, however, the following description pertains to a medical laser device and a method of operating the medical laser device to perform surgical functions.

Referring more particularly to the drawings, FIG. 1 is a pictorial diagram of a delivery system capable of transferring laser energy to a treatment site. The illustrated embodiment comprises an electromagnetic energy handpiece 20 that connects to an electromagnetic energy base unit, such as a laser base unit 30, using a linking element 25. The linking element 25 may comprise a conduit 35, which may include one or more optical fibers, tubing for air, tubing for water, and the like. The linking element 25 further may comprise a connector 40 that joins the conduit 35 to the laser base unit 30. The connector 40 may be an identification connector as is described more fully in U.S. application Ser. No. 11/192,334, filed Jul. 27, 2005 and entitled IDENTIFICATION CONNECTOR FOR A MEDICAL LASER HANDPIECE, the entire contents of which are incorporated herein by reference. The electromagnetic energy handpiece 20 may comprise an elongate portion 22 and a handpiece tip 45 formed as an extension of the elongate portion 22. The elongate portion 22 may have disposed therein a plurality of optical fibers that may connect to, or that are the same as the optical fibers included in the conduit 35. A proximal (i.e., relatively nearer to the laser base unit 30) portion 21 and a distal (i.e., relatively farther from the laser base unit 30) portion 50 may be disposed at respective proximal and distal ends of the electromagnetic energy handpiece 20. The distal portion 50 has protruding therefrom a fiber tip 55, which is described below in more detail with reference to FIG. 8. As illustrated, the linking element 25 has a first end 26 and a second end 27. The first end 26 couples to a receptacle 32 of the laser base unit 30, and the second end 27 couples to the proximal portion 21 of the electromagnetic energy handpiece 20. The connector 40 may connect mechanically to the laser base unit 30 with a threaded connection to the receptacle 32 that forms part of the laser base unit 30.

Figure 2:
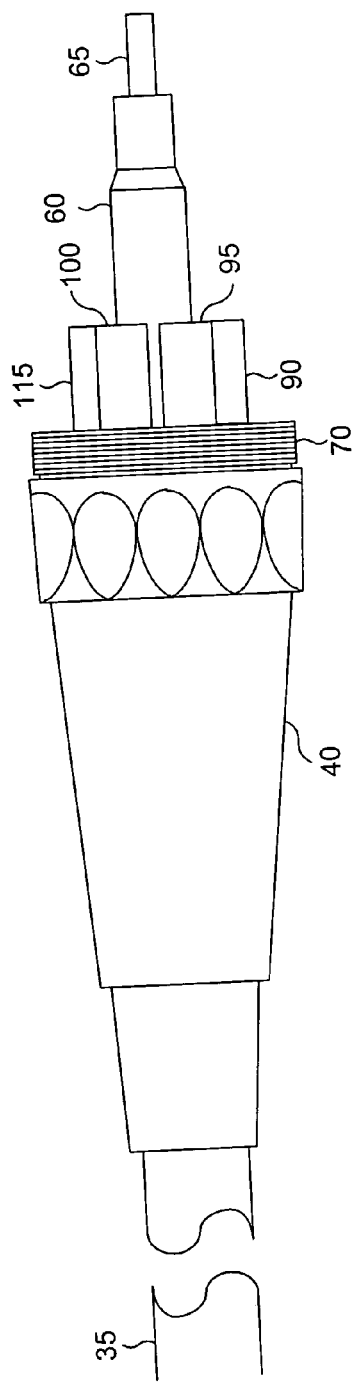
FIG. 2 is a pictorial diagram illustrating detail of a connector according to an example of the present invention.

An embodiment of a connector 40 is illustrated in greater detail in FIG. 2. The illustrated embodiment comprises a laser beam delivery guide connection 60 that may comprise, for example, a treatment optical fiber 65 capable of transmitting laser energy to the electromagnetic energy handpiece 20 (FIG. 1). The illustrated embodiment further comprises a plurality of ancillary connections comprising, in this example, a feedback connection 115, an illumination light connection 100, a spray air connection 95, and a spray water connection 90, that may connect to the laser base unit 30 (FIG. 1). The plurality of ancillary connections further may comprise connections not visible in FIG. 2 such as an excitation light connection and a cooling air connection.

The embodiment of the connector 40 illustrated in FIG. 2 further comprises a threaded portion 70 that may mate with and thereby provide for connection to the receptacle 32 on the laser base unit 30 (FIG. 1).

Figure 3:
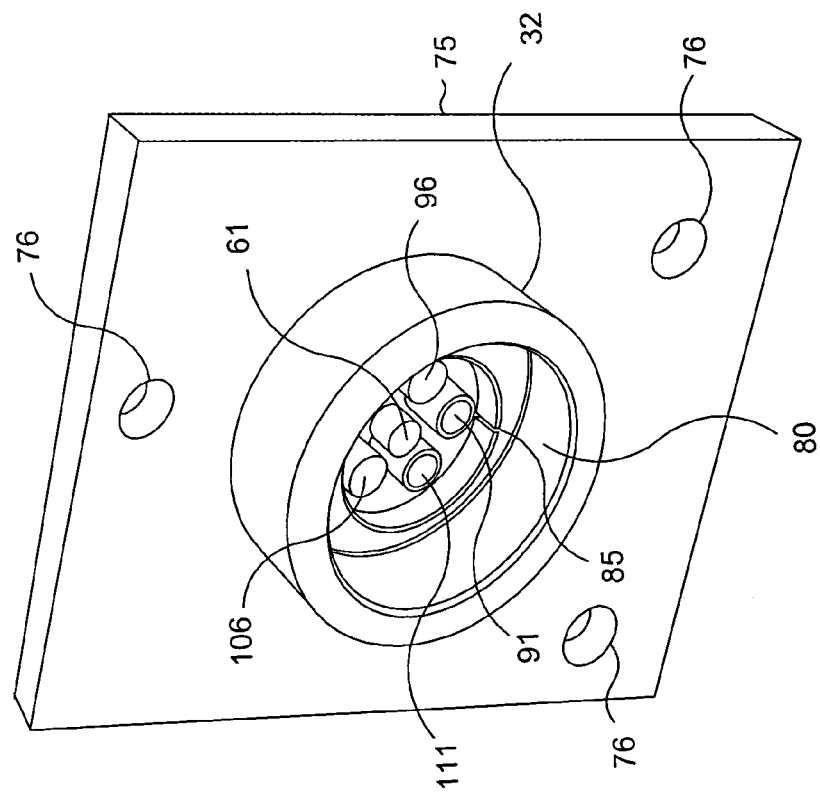
FIG. 3 is a perspective diagram of an embodiment of module that may connect to a laser base unit and that may accept the connector illustrated in FIG. 2.

FIG. 3 is a perspective diagram of an embodiment of a module that may connect to, and form a part of, a laser base unit 30 (FIG. 1) and that further may accept connector 40 (FIG. 2). The illustrated embodiment comprises a plate 75 that may fasten to a laser base unit 30 by means of, for example, screws inserted into holes 76. The module comprises a receptacle 32 that may be threaded on an inside surface 80 to mate with threads 70 on the connector 40 (FIG. 2). (Threads are not shown in FIG. 3.) The embodiment of the module further comprises a laser energy coupling 61 mated to the laser beam delivery guide connection 60 (FIG. 2), the laser energy coupling 61 being capable of providing laser energy to the delivery system. The embodiment further comprises a plurality of ancillary couplings including a spray air coupling 96, a spray water coupling 91, a cooling air coupling 111, and an excitation light coupling 106. The embodiment still further comprises a feedback coupling and an illumination light coupling that are not visible in the diagram. One or more key slots 85 may be included to assure that the connector 40 connects to the receptacle 32 in a correct orientation.

Figure 4:
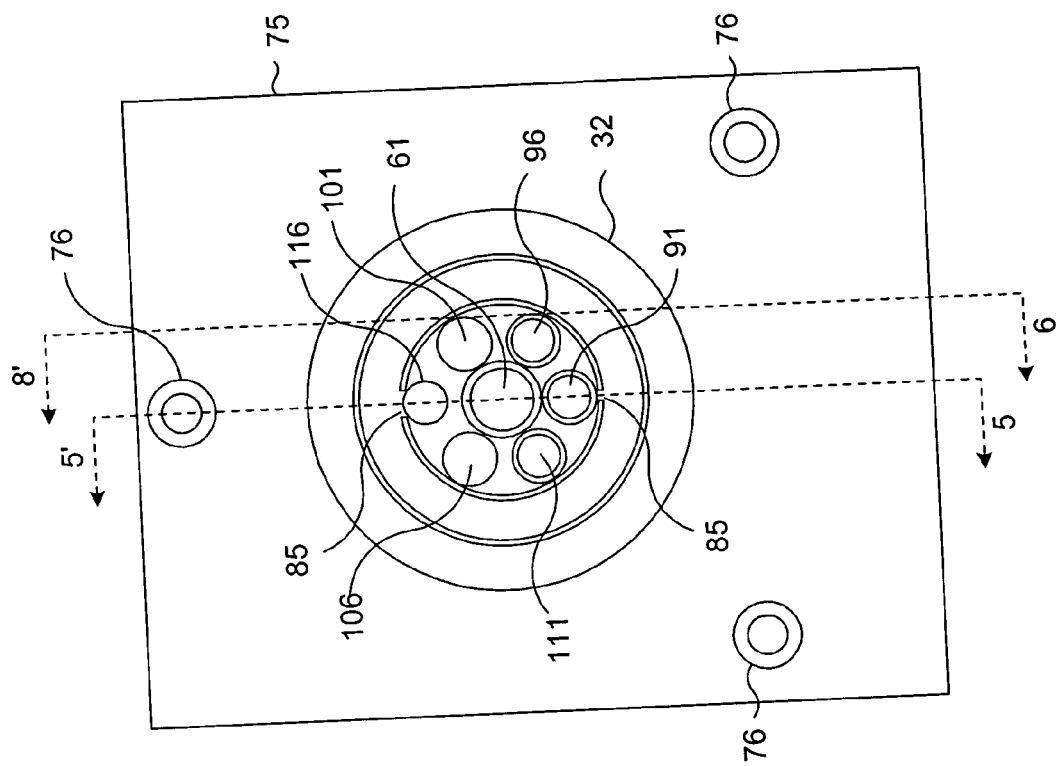
FIG. 4 is a front view of the embodiment of the module illustrated in FIG. 3.

FIG. 4 is a front view of the embodiment of the module illustrated in FIG. 3. The view in FIG. 4 illustrates the plate 75 and the holes 76 that may be used to secure the plate module to a laser base unit, such as the laser base unit 30 illustrated in FIG. 1. Further illustrated are the laser energy coupling 61, feedback coupling 116, the illumination light coupling 101, the spray air coupling 96, the spray water coupling 91, the cooling air coupling 111, and the excitation light coupling 106. In operation, the spray water coupling 91 mates with and is capable of supplying spray water to the spray water connection 90 in the connector 40 (FIG. 2). Similarly, the spray air coupling 96 mates with and is capable of supplying spray air to the spray air connection 95 in the connector 40. Additionally, the illumination light coupling 101, the excitation light coupling 106, and the cooling air coupling 111 mate with and are capable of supplying, respectively, illumination light to the illumination light connection 100, excitation light to the excitation light connector(not shown), and cooling air to the cooling air connection (not shown) in the connector 40. Further, the feedback coupling 116 mates with and is capable of receiving feedback from the feedback connection 115 in the connector 40. According to an illustrative embodiment, the illumination light coupling 101 and the excitation light coupling 106 couple light from a light-emitting diode (LED) or a laser light source to, respectively, the illumination light connection 100 and the excitation light connection (not shown). One embodiment employs two white LEDs as a source for illumination light. Also illustrated in FIG. 4 are key slots 85 that may prevent the connector 40 from being connected to the receptacle 32 in an incorrect orientation.

Figure 5:
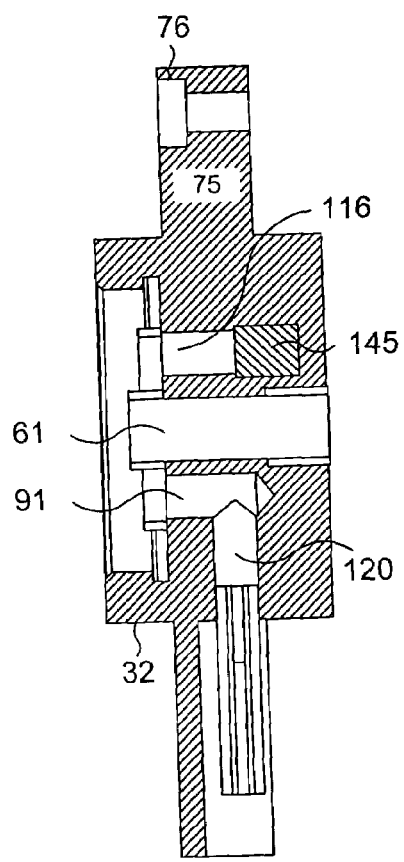
FIG. 5 is a cross-sectional view of the module illustrated in FIG. 4, the cross-section being taken along a line 5-5' of FIG. 4.

FIG. 5 is a cross-sectional view of the module illustrated in FIGS. 3 and 4. The cross-section is taken along line 5-5' of FIG. 4, the line 5-5' showing cross-sections of the laser energy coupling 61, the feedback coupling 116, and the spray water coupling 91. A water source 120 may supply water to the spray water coupling 91.

Figure 6:
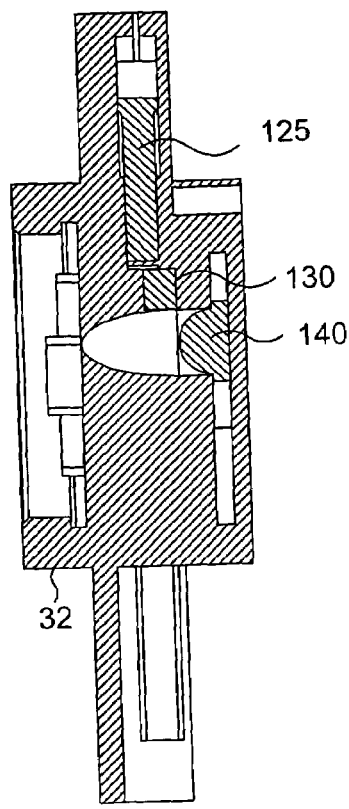
FIG. 6 is another cross-sectional view of the module illustrated in FIG. 4, the cross-section being taken along a line 6-6' of FIG. 4.

FIG. 6 is another cross-sectional view of the module illustrated in FIGS. 3 and 4. The cross-section of FIG. 6 is taken along line 6-6' of FIG. 4. The diagram depicts cross-sections of a light source (e.g., an LED 140) that may be capable of supplying light to, for example, one or both of the illumination light coupling 101 (FIG. 4) and the excitation light coupling 106. A pneumatic shutter 125 may control a position of a radiation filter 130 disposed in the laser base unit 30 so that the filter is either inserted or removed from a light path originating with the light source (e.g., the LED 140). For example, one or more pneumatic shutter filters may be provided that enable switching between, for example, blue and white light that is coupled to the illumination light coupling 101 and the excitation light coupling 106 in order to enhance excitation and visualization.

Figure 7:
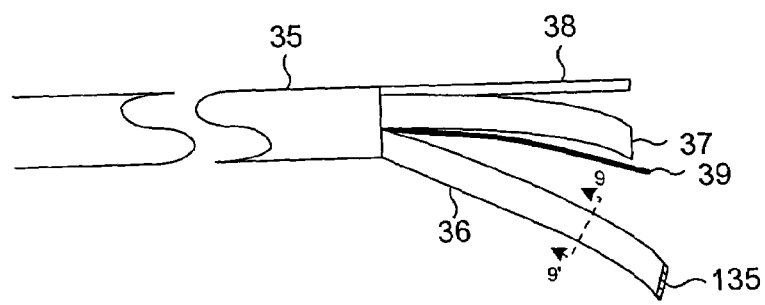
FIG. 7 is a pictorial diagram of an embodiment of the conduit shown in FIG. 1.

FIG. 7 is a pictorial diagram of an embodiment of the conduit 35 shown in FIG. 1. The illustrated embodiment of the conduit 35 comprises a plurality of proximal members, such as, four proximal members comprising first proximal member 36, second proximal member 37, third proximal member 38, and fourth proximal member 39. First, second, and third proximal members 36, 37, and 38 may have hollow interiors configured to accommodate one or more light transmitters or other tubular or elongate structures that have cross-sectional areas less than a cross-sectional area of a hollow interior of the conduit 35. According to one embodiment, first proximal member 36 comprises an illumination fiber, second proximal member 37 comprises an excitation fiber, and third proximal member 38 comprises a feedback fiber. First, second, and third proximal members 36, 37, and 38 may be arranged such that the hollow interior of each proximal member is in communication with a hollow interior of elongate body 22 (FIG. 1). This arrangement provides for a substantially continuous path for the light transmitters to extend from the proximal portion 21 to the distal portion 50 of the electromagnetic energy handpiece 20.

In accordance with an aspect of the present invention, the third proximal member 38 may be configured to receive feedback (e.g., reflected or scattered light) from the electromagnetic energy handpiece 20 and may transmit the feedback to the laser base unit 30. Waveguides carried by the third proximal member may be positioned to surround a treatment optical fiber 400 (FIG. 8, infra) at an output or distal end 50 of the electromagnetic energy handpiece as is more particularly described below.

The fourth proximal member 39 may comprise a laser energy fiber that receives laser energy derived from an erbium, chromium, yttrium, scandium, gallium, garnet (Er, Cr:YSGG) solid state laser disposed in the laser base unit 30 (FIG. 1). The laser may generate laser energy having a wavelength of approximately 2.78 microns at an average power of about 6 W, a repetition rate of about 20 Hz, and a pulse width of about 150 microseconds. Moreover, the laser energy may further comprise an aiming beam, such as light having a wavelength of about 655 nm and an average power of about 1 mW transmitted in a continuous-wave (CW) mode. The fourth proximal member 39 may be coupled to or may comprise the treatment optical fiber 65 (FIG. 2) that receives laser energy from the laser energy coupling 61 (FIG. 4). The fourth proximal member 39 further may transmit the laser energy received from the laser base unit 30 to the distal portion 50 of the electromagnetic energy handpiece 20 (FIG. 1).

Although the illustrated embodiment is provided with four proximal members, a greater or fewer number of proximal members may be provided in additional embodiments according to, for example, the number of light transmitters provided by the laser base unit 30. In addition, the illustrated embodiment includes first and second proximal members 36 and 37 that have substantially equal diameters and a third proximal member 38 that has a diameter less than either of the diameters of the first and second proximal members 36 and 37. Other configurations of diameters are also contemplated by the present invention. In an exemplary embodiment, the proximal members connect with the connections in the connector 40 illustrated in FIG. 2. For example, the first proximal member 36 may connect with the illumination light connection 100 and the second proximal member 36 may connect with the excitation light connection (not shown). The third proximal member 38 may connect with the feedback connection 115, and the fourth proximal member 39 may connect with the laser beam delivery guide connection 60 and the treatment optical fiber 65. Attachment of the proximal members 36-39 to the connections may be made internal to connector 40 in a manner known or apparent to those skilled in the art in view of this disclosure and is not illustrated in FIGS. 2 and 7.

Figure 8:
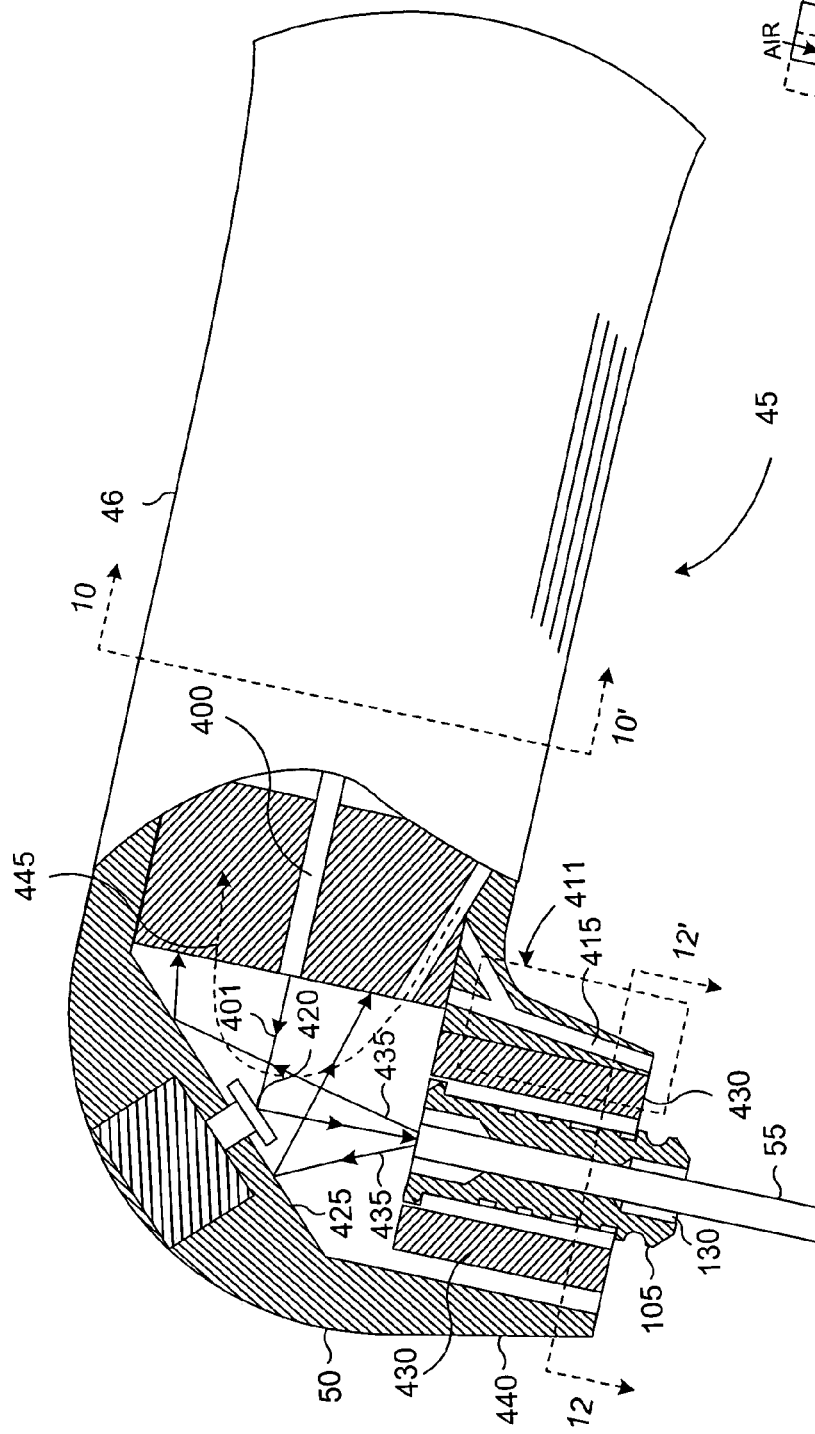
FIG. 8 is a partial cut-away diagram of a handpiece tip in accordance with an example of the present invention.

FIG. 8 is a partial cut-away diagram of a handpiece tip 45 (cf. FIG. 1) that couples with the laser base unit 30 by means of the linking element 25 and the elongate portion 22 of the electromagnetic energy handpiece 20. The illustrated embodiment, which is enclosed by an outer surface 46, may receive electromagnetic (e.g., laser) energy, illumination light, excitation light and the like from the laser base unit 30. Typically, the laser energy and light are received by proximal members 36-39 (FIG. 7) as described above and transmitted through waveguides, such as fibers 405 disposed in the elongate portion 22 and the handpiece tip 45 as described below with reference to FIG. 10. For example, illumination light (not shown) may be received by the handpiece tip 45, such as from proximal members 36 and 37 (FIG. 7), carried by fibers 405 (FIG. 10, not shown in FIG. 8), and directed toward a first mirror 425 disposed within the distal portion 50 of the electromagnetic energy handpiece 20. The first mirror 425 in the illustrated embodiment directs illumination light toward a plurality of tip waveguides 430 as is more particularly described below with reference to FIG. 12. Illumination light exiting the tip waveguides 430 may illuminate a target area.

According to one embodiment, concentrated electromagnetic energy, such as laser energy 401, is received (e.g., through fourth proximal member 39 (FIG. 7)) and carried by an internal waveguide such as a treatment optical fiber 400. The laser energy 401 may be directed toward a second mirror 420, which may eclipse at least a part of the first mirror 425 relative to a direction of propagation of the illumination light to the first mirror 425, the second mirror 420 likewise being disposed in the distal portion 50 of the electromagnetic energy handpiece 20. The second mirror 420 may reflect, and thereby direct, the laser energy 401 toward the fiber tip 55. Relative to the concentrated electromagnetic energy (e.g., laser energy 401), the illumination light may comprise an example of additional electromagnetic energy, so described because the illumination light and/or, as described below, excitation light, may comprise electromagnetic energy exhibiting a relatively low power level that is directed to illuminate a portion of a target surface that may, for example, surround a portion of a target surface to which the concentrated electromagnetic energy is directed. The concentrated electromagnetic energy (e.g., laser energy 401) may be directed toward the target surface by the fiber tip 55.

In some embodiments, respective first and second mirrors 425 and 420 may comprise parabolic, toroidal, and/or flat surfaces. FIG. 8 also illustrates a simplified view of a path 445 of cooling air received from a cooling air line (not shown) in the handpiece that may receive cooling air from the cooling air coupling 111 (FIG. 4).

The fiber tip 55 illustrated in FIG. 8 may be encased in a tip ferrule 105 having a distal end. The tip ferrule 105, together with the fiber tip 55, may form a removable, interchangeable unit as is described more fully in U.S. Provisional No. 60/610,757, filed Sep. 17, 2004 and entitled, OUTPUT ATTACHMENTS CODED FOR USE WITH ELECTROMAGNETIC-ENERGY PROCEDURAL DEVICE, the entire contents of which are included herein by reference to the extent not mutually incompatible.

Figure 9:
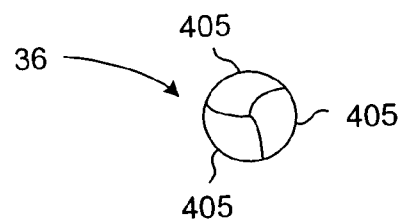
FIG. 9 is a sectional view of a proximal member of FIG. 7 taken along line 9-9' of FIG. 7.

FIG. 9 is a cross-sectional view of first proximal member 36 taken along line 9-9' of FIG. 7 demonstrating that first proximal member 36 (as well as, optionally, second proximal member 37) may comprise three optical fibers 405 substantially fused together to define a unitary light emitting assembly or waveguide. In modified embodiments, the three optical fibers 405 may be joined by other means or not joined. According to other embodiments, one or more of the proximal members, such as the second proximal member 37, can include different numbers of optical fibers 405. In an illustrated embodiment, the second proximal member 37 can include six optical fibers 405 (FIG. 9) that begin to separate and eventually (e.g., at line 10-10' in FIG. 8) surround a laser energy waveguide, such as treatment optical fiber 400, as illustrated in a cross-sectional view of FIG. 10 taken along line 10-10' of FIG. 8 in the handpiece tip 45. In another exemplary embodiment, the second proximal member 37 can include three optical fibers 405 (FIG. 9) and the first proximal member 36 can include three optical fibers 405 (FIG. 9), all six of which begin to separate and eventually (e.g., at line 10-10' in FIG. 8) surround a laser energy waveguide, such as treatment optical fiber 400 in the handpiece tip 45.

Figure 10:
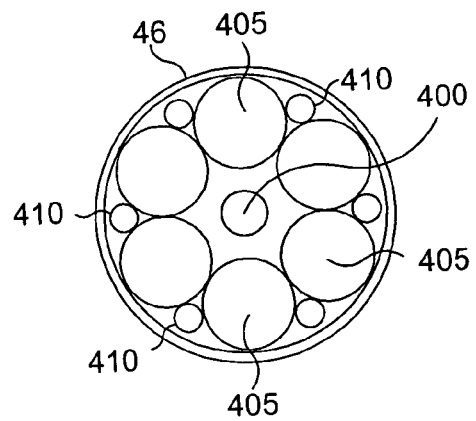
FIG. 10 is a cross-sectional view of a handpiece tip taken along line 10-10' of FIG. 8.
Figure 11:
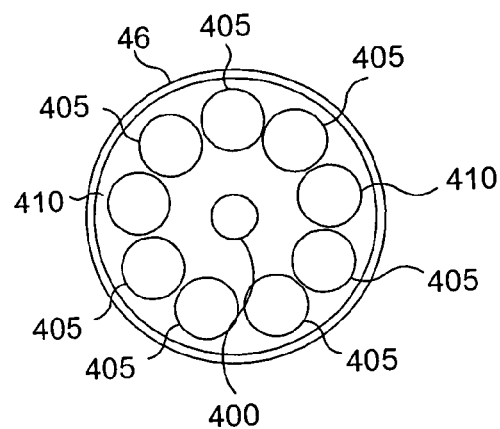
FIG. 11 is a cross-sectional diagram of another embodiment of the handpiece tip taken along the line 10-10' of FIG. 8.

FIG. 11 is a cross-sectional diagram of another embodiment of the handpiece tip 45, the cross-section being taken along line 10-10' in FIG. 8. FIG. 11 depicts a laser energy waveguide, such as treatment optical fiber 400 surrounded by illumination waveguides, such as fibers 405, and feedback waveguides, such as fibers 410, all of which are disposed within outer surface 46. In a manner similar to that described above with reference to FIG. 10, the illumination waveguides, such as fibers 405 may receive light energy from the laser base unit 30 (FIG. 1) by way of illumination light coupling 101 (FIG. 4), illumination light connection 100 (FIG. 2), and, for example, proximal members 36 and/or 37 (FIG. 7); and fibers 405 may direct the light to the distal portion 50 of the electromagnetic energy handpiece 20 (FIG. 8). In modified implementations such as those involving, for example, caries detection, one or more fibers (e.g., fibers 405) may function as illumination, excitation and/or feedback waveguides.

Continuing reference with reference to FIG. 7 and related figures, the third proximal member 38 may include six relatively smaller fibers 410, as likewise is shown in the cross-sectional view of FIG. 10. The smaller fibers 410 and/or other additional waveguides may be disposed within the outer surface 46. Fibers 410 are illustrated as being separate from each other, but in additional embodiments two or more of the fibers 410 may be fused or otherwise joined together. Fibers 405 and 410 can be manufactured from plastic using conventional techniques, such as extrusion and the like.

According to an aspect of the present invention, the fibers 410 can be configured to receive feedback (e.g., reflected or scattered light) from the electromagnetic energy handpiece 20. Fibers 410 may be positioned to surround a treatment optical fiber 400 (FIG. 8, infra) at an output or distal end 50 of the electromagnetic energy handpiece. In a particular implementation the fibers 410 can be configured to receive feedback from the target surface, while in modified implementations the fibers 410 may additionally or alternatively be configured to receive feedback from components (e.g., optical components) within the electromagnetic energy handpiece. For example, a modified implementation may comprise feedback in the form of scattered light 435 (FIG. 8) received from the fiber tip 55. As presently embodied, the fibers 410 are positioned to transmit the received feedback through the third proximal member 38 and to the laser base unit 30 (FIG. 1).

Feedback waveguides, such as fibers 410, may receive feedback light from the fiber tip 55 (FIG. 8) and may transmit the feedback light to third proximal member 38, which couples to or comprises feedback connection 115. The feedback light may be received by the feedback coupling 116, which transmits the light to a feedback detector 145 (FIG. 5) disposed in the laser base unit 30 (FIG. 1). In other embodiments, such as described more fully in the above-referenced U.S. application Ser. No. 11/192,334 entitled IDENTIFICATION CONNECTOR FOR A MEDICAL LASER HANDPIECE, the laser base unit 30 may additionally supply spray air, spray water, and cooling air to the electromagnetic energy handpiece 20.

Figure 12:
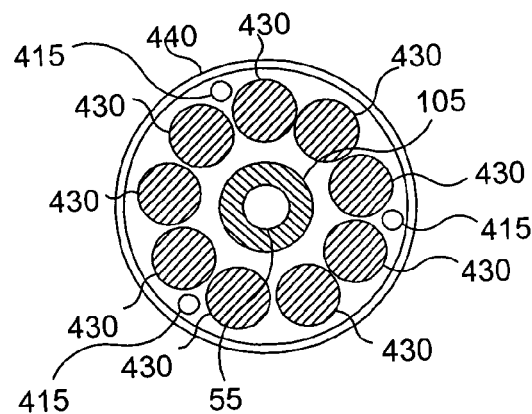
FIG. 12 is a cross-sectional diagram of another embodiment of the electromagnetic energy handpiece tip taken along line 12-12' of FIG. 8.

FIG. 12 is a cross-sectional diagram of another embodiment of the electromagnetic energy handpiece tip 45 taken along line 12-12' of FIG. 8. This embodiment illustrates a fiber tip 55 surrounded by a tip ferrule or sleeve 105, and, optionally, glue that fills a cavity 130 around the fiber tip 55 to hold the fiber tip 55 in place. Tip waveguides 430 may receive illumination light from first mirror 425 (FIG. 8) and direct the illumination light to a target. In some embodiments, fluid outputs 415, which are disposed in the handpiece tip 45, may carry, for example, air and water. More particularly, illumination light exiting from the illumination fibers 405 (cf. FIG. 11) is reflected by first mirror 425 (FIG. 8) into the tip waveguides 430 (FIGS. 8 and 12). While a portion of this illumination light may also be reflected by first mirror 425 (FIG. 8) into fiber tip 55, fiber tip 55 receives, primarily, a relatively high level of laser energy 401 from treatment optical fiber 400 (cf. FIG. 11), which laser energy, as presently embodied, comprises radiation including both a cutting beam and an aiming beam. In a representative embodiment, illumination light from the illumination fibers 405 that exits the tip waveguides 430 is white light of variable intensity (e.g., adjustable by a user) for facilitating viewing and close examination of individual places of a target surface, such as a tooth. For example, a cavity in a tooth may be closely examined and treated with the aid of light from a plurality of tip waveguides 430.

Figure 8A:
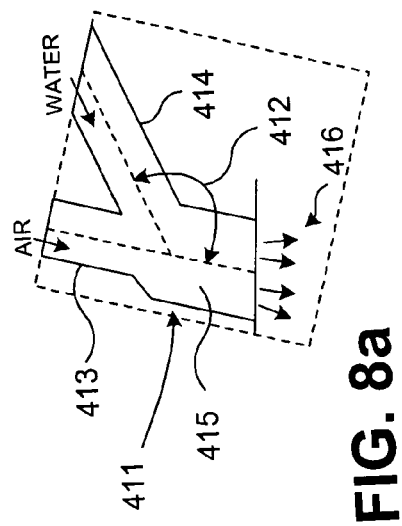
FIG. 8a is a pictorial diagram of detail of the handpiece tip of FIG. 8 illustrating a mixing chamber for spray air and water.

A detailed illustration of an embodiment of a chamber for mixing spray air and spray water in the handpiece tip 45 is shown in FIG. 8a. As illustrated, the mixing chamber comprises an air intake 413 connected to, for example, tubing (e.g., a spray air line, not shown) that connects to and receives air from, the spray air connection 95 in the connector 40 (FIG. 2). Similarly, a water intake 414 may connect to tubing (also not shown) that connects to and receives water from the spray water connection 90 in the connector 40 (FIG. 2). The air intake 413 and the water intake 414, which may have circular cross-sections about 250 μm in diameter, join at an angle 412 that may approximate 110° in a typical embodiment. Mixing may occur in a neighborhood where the air intake 413 and water intake 414 join, and a spray (e.g., atomized) mixture 416 of water and air may be ejected through a fluid output 415. The embodiment illustrated in FIG. 12 depicts three fluid outputs 415. These fluid outputs may, for example, correspond to, comprise parts of, or comprise substantially all of, any of fluid outputs described in U.S. application Ser. No. 11/042,824, filed Jan. 24, 2005 and entitled ELECTROMAGNETICALLY INDUCED TREATMENT DEVICES AND METHODS, the entire contents of which are incorporated herein by reference, to the extent compatible, or, in other embodiments, structures described in the referenced provisional patent application may be modified to be compatible with the present invention. The fluid outputs 415 may, as illustrated in FIGS. 8 and 12, have circular cross-sections measuring about 350 μm in diameter.

Scattering of light as described above with reference to FIG. 7 can be detected and analyzed to monitor various conditions. For example, scattering of an aiming beam can be detected and analyzed to monitor, for example, integrity of optical components that transmit the cutting and aiming beams. In typical implementations the aiming beam may cause little to no reflection back into the feedback fibers 410. However, if any components (such as, for example, second mirror 420 or fiber tip 55) is damaged, scattering of the aiming beam light (which may be red in exemplary embodiments) may occur. Scattered light 435 (FIG. 8) may be directed by the first mirror 425 into feedback fibers 410 that may convey the scattered light to the laser base unit 30 (FIG. 1).

In accordance with an aspect of the present invention, scattering of light as described above with reference to FIG. 7 can also be used for detection of various conditions, such as dental caries.

Figure 13:
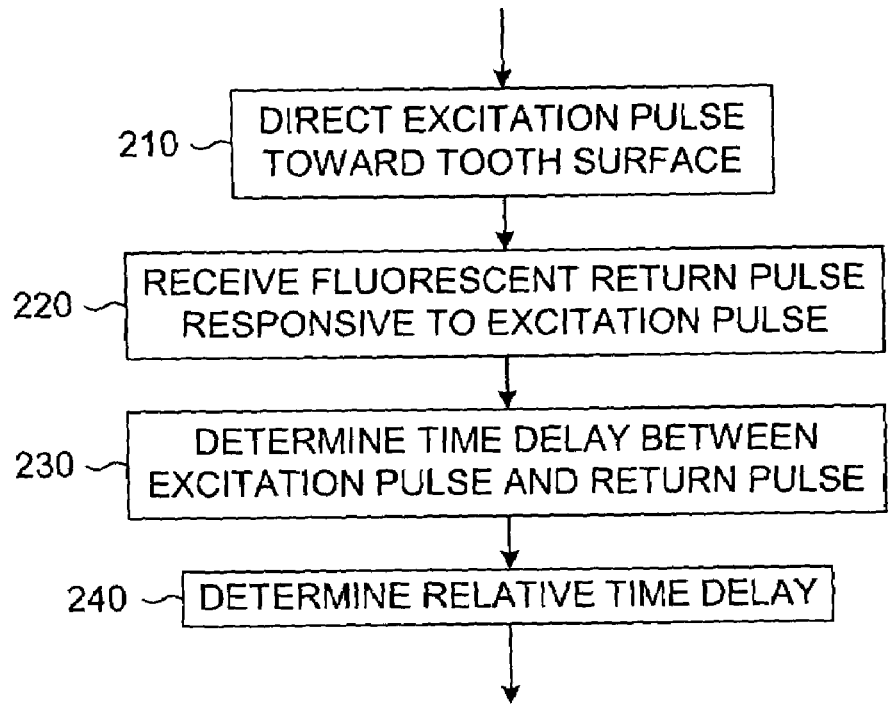
FIG. 13 is a flow diagram depicting an implementation of a method of detecting dental caries according to an implementation of the present invention.

FIG. 13 is a flow diagram that introduces an implementation of a method of detecting dental caries according to the present invention. According to the illustrated implementation, an excitation pulse of light is directed toward a tooth surface at step 210. For example, for caries detection, illumination light may be received from the laser base unit 30 as already described. The illumination light may be transmitted through and emitted from the illumination and/or excitation fibers 405 (FIGS. 10 and 11) as an excitation pulse in a spectral range (e.g., range of violet, blue, cyan, green, and yellow light) from about 360 nm to about 580 nm. In a modified embodiment, monochromatic light having a wavelength of, for example, about 406 nm (e.g., visible violet wavelengths) can be used instead. Other spectral frequencies or ranges may be used in other modified embodiments, as well.

A source of the light used for caries detection can comprise, according to one embodiment, white light received from at least one white light emitting diode such as LED 140 (FIG. 6), which is disposed in the laser base unit 30 and the output of which may or may not be coupled to a filter as described herein. In other embodiments at least one light source may comprise a source such as a mercury-vapor lamp, a krypton laser, a halogen lamp, or a dye laser as representative examples. According to another implementation, the LED 140 may emit another type of light (e.g., blue light), which can then be filtered to obtain a desired light output (e.g., white light, or light having a wavelength in a range of about 360 nm to about 420 nm). Accordingly, in typical implementations at least one corresponding light filter 135 (FIG. 7) can be disposed in the path of the radiation generated by the at least one light source to pass only desired wavelengths of, in an illustrated embodiment, about 360 nm to about 420 nm. Although shown coupled to the first proximal member 36 (FIG. 7), light filter 130 or 135 may additionally or alternatively be coupled to the second proximal member 37 (FIG. 7). In another embodiment, a light filter 130 controlled by a pneumatic shutter 125 can be disposed in the laser base unit 30. The pneumatic shutter 125 can cause the filter 130 to be inserted into or removed from a light path originating with the light source (e.g., LED 140), the light path continuing through, for example, the second proximal member 37 (FIG. 7). According to yet another embodiment, the pneumatic shutter 125 may switch between white light and any other (filtered) of light.

With reference to the cross-sectional view of FIG. 6, one implementation that comprises LED 140 for directing light through pneumatically-controlled shutter filter 130 can supply light to, for example, excitation light coupling 106 (FIG. 4). The excitation light coupling 106 is capable of coupling light into an excitation light connection disposed in the connector 40 of FIG. 2, although the excitation light connection is not visible in the view shown in FIG. 2. According to an exemplary embodiment, the second proximal member 37 (FIG. 7) receives light from the excitation light connection and transmits the light to first mirror 425 (FIG. 8) in the distal portion 50 of the electromagnetic energy handpiece 20. Light reflected from the first mirror 425 may be directed to, for example, tip waveguides 430 as illustrated in FIGS. 8 and 12. An LED similar to LED 140 (FIG. 6) may direct light into the illumination light coupling 101 (FIG. 4). The illumination light coupling 101 may connect with and couple light into the illumination light connection 100 in the connector 40 illustrated in FIG. 2. Illumination light connection 100 may direct the light to, for example, first proximal member 36 (FIG. 7), which transmits the light to the first mirror 425 (FIG. 8), whence the excitation light is directed to tip waveguides 430 (FIGS. 8 and 12). A light source (e.g., LED 140) for the excitation coupling 106 can be of a different type from that of a light source for the illumination light coupling 101, or the sources can be of the same type.

In accordance with one aspect of the present invention, light entering the excitation light coupling 106 is pulsed, wherein the pulse duration may range from about 0.001 to 100 μs. In a representative embodiment, the pulse duration may be about 1 μs. The radiation may comprise a sequence of identical pulses, or may comprise sequences of varying predetermined pulse shapes, spacings and/or durations according to desired applications in order to facilitate detection and analysis of caries and/or other properties of the tooth by way of returned radiation therefrom according to signal analysis techniques known to those skilled in the art.

According to one embodiment, both illumination and excitation light sources comprise white-light LEDs but only the radiation entering into the excitation light coupling 106 is processed to produce light (e.g., violet light) in a spectral range of about 360 nm to about 420 nm, the light being pulsed as described above. In another embodiment, the illumination light coupling 101 of FIG. 4 also transmits as an excitation light coupling, so that two excitation fibers (e.g., first proximal member 36 and second proximal member 37) direct excitation radiation (e.g., filtered and/or pulsed radiation) from the laser base unit 30 toward the handpiece 20.

Returning to FIG. 13, carious places of a tooth issue fluorescent radiation (e.g., visible red wavelengths) in response to incident radiation from an excitation pulse. This fluorescent return pulse is received at step 220. More particularly, the fluorescent return pulse may be received by, for example, the tip waveguides 430 (FIGS. 8 and 12). The fluorescent return pulse may permit identification of different types/strains of caries-causing bacteria that return radiation of different (e.g., varying hues of red) fluorescent wavelengths. The fluorescent radiation can differ in one or more of intensity, delay and spectral distribution from radiation returned by a healthy tooth, which radiation may comprise, for example, visible green wavelengths. Thus, carious places of the tooth may appear as bright spots that stand out clearly when displayed against a dark background. Accordingly, a condition of carious disease can be detected with a relatively high level of accuracy and reliability, at a relatively early stage.

Radiation returned from a surface of the tooth as a result of reflection and fluorescence enters the tip waveguides 430 (FIGS. 8 and 12) of the handpiece 20 (FIG. 1) for processing. Details regarding, for example, generation of excitation light and processing of returned radiation to, for example, remove background noise and facilitate qualitative and quantitative detection of caries, are described in U.S. Pat. No. 5,306,144, entitled DEVICE FOR DETECTING DENTAL CARIES, the entire contents of which are incorporated herein by reference to the extent compatible with, or modifiable by one skilled in the art to be compatible with, or to the extent not mutually exclusive with, the disclosure herein.

In an exemplary embodiment, returned radiation received by the feedback coupling 116 (FIG. 6) is processed by a first filter (not shown) within the laser base unit 30 (FIG. 1), the first filter passing radiation in a spectral range above 620 nm (e.g., above orange light). The radiation passed by the first filter is thus restricted at a lower end, and so contains mainly fluorescent radiation relatively devoid of interfering background radiation having shorter wavelengths.

Wavelengths above an acceptance wavelength of the filter reach the photo detector 145 (FIG. 5) within the laser base unit 30. The photo detector 145 is connected to receive filtered radiation from the first filter and to convert the filtered radiation into a first electrical signal for quantitative evaluation. The first electrical signal, which can be indicated in a known manner, is in an illustrated embodiment approximately proportional to a level of radiation intensity detected by the photo detector 145 and is thus suitable for use in quantitative assessment of an extent of a detected caries condition. Consequently, carious places of the tooth can be analyzed.

In one embodiment, the first filter is a narrow band filter that accepts radiation returned from the tooth at wavelengths of about 636 nm (corresponding to visible red light). A second narrow band filter is also provided that accepts radiation returned from the tooth at wavelengths of about 550 nm (corresponding to visible green light), which is a peak reflectance wavelength from healthy tooth tissue. The photo detector 145 or another photo detector converts the filtered radiation from the second narrow band filter into a second electrical signal. A quotient formed by dividing the first electrical signal by the second electrical can be automatically determined within the laser base unit 30, and the quotient can be used to provide an indication of a presence of caries. Stated otherwise, a magnitude of a green peak can be compared to a magnitude of a red peak to determine the presence and extent of caries.

Figure 14:
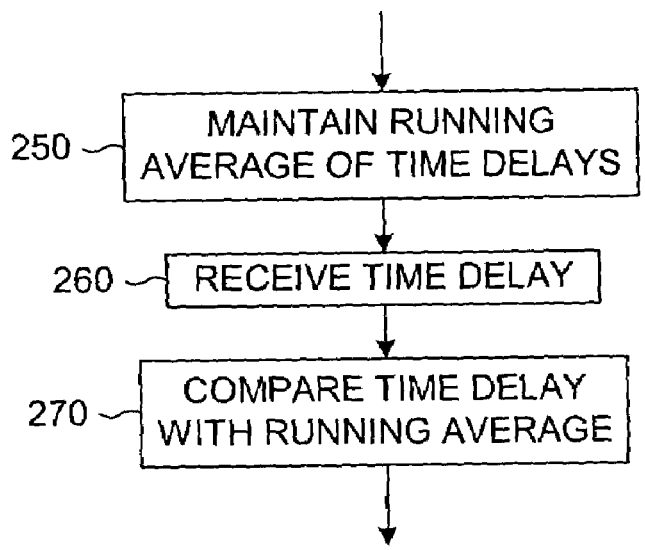
FIG. 14 is a flow diagram illustrating a technique for determining a relative time delay in accordance with an example of the present invention.

As presently embodied, a time delay is detected between a given excitation pulse and a corresponding returned pulse at step 230 of the implementation of the method of the present invention depicted in FIG. 13. A relative time delay may also be determined at step 240 of the same figure. FIG. 14 is a flow diagram illustrating an implementation of a method of determining relative time delays. According to this implementation of the method of the present invention, a running average of delays between excitation pulses and corresponding returned pulses is maintained at step 250. A time delay associated with an excitation pulse is received at step 260, and the time delay between a given excitation pulse and the corresponding return pulse is compared with the running average of delays at step 270. In other embodiments, an excitation pulse may be compared with a corresponding return pulse for differences in at least one of intensity, delay and spectral distribution. A given time delay (and/or another difference or other differences) between an excitation pulse and a corresponding return (e.g., fluorescence) pulse can provide an indication of a depth of caries, wherein a deeper (e.g., sub-surface) caries may have a greater delay and/or greater scattering than the scattering associated with surface caries or healthy tissue. Different lengths of excitation pulses may be able to facilitate the ascertainment of different types of information pertaining to the tooth surface. A more wide-spread caries on a tooth surface may result in, for example, a return pulse having a longer fluorescence time when compared with less widely distributed caries. Also, a presence of different types of bacteria may be detected to an extent that different types of bacteria affect one or more characteristics of a return pulse differently. For instance, different types of bacteria may have different delay or fluorescence times.

In addition to caries detection, the cutting beam radiation, which, generally, carries a relatively higher power than that of the illumination or excitation light, the cutting beam being emitted from fiber tip 55 of the handpiece tip 45, can be used for caries therapy. In such a case, cutting beam radiation having a wavelength (e.g., violet light wavelength) in a range from about 360 m to about 420 nm may cause caries pathogens to react sensitively to cutting beam radiation and to die off. Early-stage dental caries treatment with simultaneous observation of the location of the treatment (e.g., in an iterative fashion, with multiple iterations being performed) may thus be implemented.

In one embodiment, the tip waveguides 430 (FIGS. 8 and 12) and tip ferrule or sleeve 105 are housed (e.g., supported) in a housing 440 (FIG. 12) that may comprise, for example, metal. According to one implementation, an interior of the housing 440 is solid, with cavities disposed therein for accommodating, for example, the tip ferrule or sleeve 105, and tip waveguides 430, and for defining the fluid outputs 415. In other implementations, the housing 440 and/or interior can comprise a transparent material, such as a transparent plastic, sapphire, or quartz, so that the individual tip waveguides 430 may optionally be omitted. Thus, in some embodiments, light can be transmitted through the transparent material of the interior without a need for disposing or defining tip waveguides 430, so that the interior may comprise cavities only for the tip ferrule of sleeve 105, and the fluid outputs 415.

Returning to FIG. 11, the illustrated embodiment comprises a laser emitting fiber 400 surrounded by six fibers 405, which may be used for illumination and excitation in implementations involving caries detection, and three feedback fibers 410. The fibers 405 may be referred to as illumination/excitation fibers. In other embodiments, greater or fewer numbers, or different dimensions or spacings, of the illumination/excitation fibers 405 (and/or tip waveguides 430) and/or feedback fibers 410 may be employed.

According to one aspect of the invention, two or more of each, and in a particular implementation three or more of each, may be used to avoid, for example, shading, which may result from using only a single (or two) illumination/excitation fibers 405 and/or tip waveguides 430.

In a representative embodiment, the fluid outputs 415 (FIG. 12) are spaced at zero (a first reference), one hundred twenty, and two hundred forty degrees. In another embodiment, the six illumination/excitation fibers 405 and three feedback fibers 410 (FIG. 11) are optically aligned with and coupled via first mirror 425, for example, on a one-to-one basis, to nine tip waveguides 430 (FIGS. 8 and 12). For example, if nine elements (e.g., six illumination/excitation fibers 405 and three feedback fibers 410) are evenly spaced and disposed at zero (a second reference, which may be the same as or different from the first reference), forty, eighty, one hundred twenty, one hundred sixty, two hundred, two hundred forty, two hundred eighty, and three hundred twenty degrees, then nine tip waveguides 430 may likewise be evenly spaced and disposed at zero, forty, eighty, one hundred twenty, one hundred sixty, two hundred, two hundred forty, two hundred eighty, and three hundred twenty degrees. In another embodiment wherein, for example, the tip waveguides 430 are arranged in relatively closely-spaced groups of three with each group being disposed between two fluid outputs, the tip waveguides 430 may be disposed at, for example, about zero, thirty-five, seventy, one hundred twenty, one hundred fifty-five, one hundred ninety, two hundred forty, two hundred seventy-five, and three hundred ten degrees. In one such embodiment, the tip waveguides 430 may likewise be disposed at about zero, thirty-five, seventy, one hundred twenty, one hundred fifty-five, one hundred ninety, two hundred forty, two hundred seventy-five, and three hundred ten degrees. Further, in such an embodiment, the fluid outputs may be disposed between the groups of tip waveguides at about ninety-five, two hundred fifteen, and three hundred thirty-five degrees.

The cross-sectional views of FIGS. 10 and 11 may alternatively (or additionally), without being changed, correspond to cross-sectional lines 10-10' taken in FIG. 8 closer to (or next to) first and second mirrors 425 and 420 to elucidate corresponding structure that outputs radiation distally onto the first mirror 425 and the second mirror 420. The diameters of illumination/excitation fibers 405 and feedback fibers 410 may be different as illustrated in FIG. 10 or the diameters may be the same or substantially the same as shown in FIG. 11. In an exemplary embodiment, the illumination/excitation fibers 405 and feedback fibers 410 in FIG. 11 comprise plastic constructions with diameters of about 1 mm, and the tip waveguides 430 in FIGS. 8 and 12 comprise sapphire constructions with diameters of about 0.9 mm.

Figure 15:
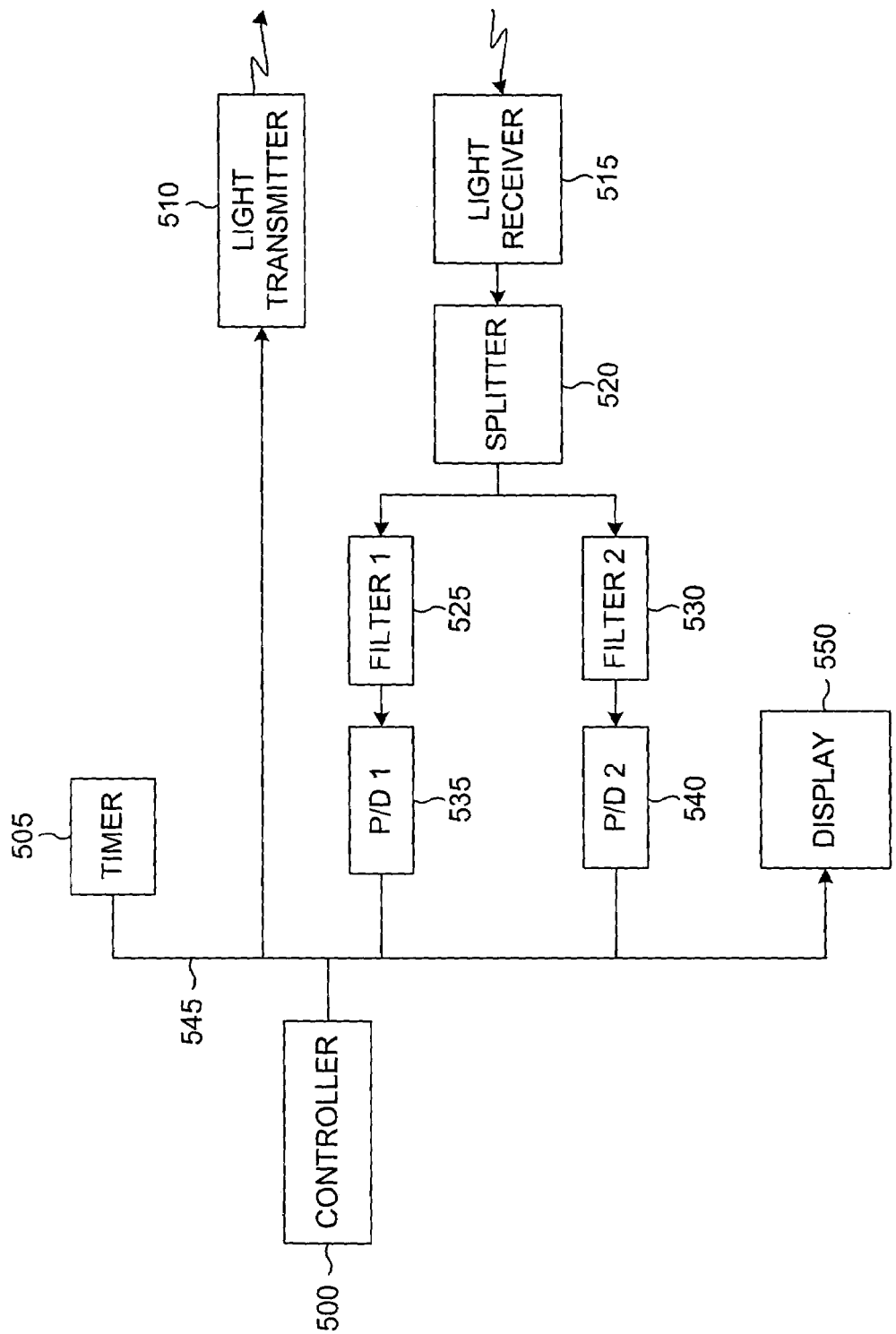
FIG. 15 is a block diagram of a portion of an exemplary apparatus that may be used to detect dental caries according to an implementation of the present invention.

FIG. 15 is a block diagram of a portion of an embodiment of an apparatus that may be used to detect dental caries. The illustrated embodiment, which may be disposed within a laser base unit 30 (FIG. 1) comprises a controller 500, a timer 505, a light transmitter 510, and a light receiver 515. The embodiment further comprises a light splitter 520, a first light filter 525, a second light-filter 530, a first photo detector 535, a second photo detector 540, and a display device 550. A system bus 545 provides a communication and control path by means of which the controller 500 is able to control the timer 505 and the light transmitter 510. The system bus 545 further provides means for the controller 500 to receive electrical signals from first and second photo detectors 535 and 540 and to communicate with the display device 550.

In operation the controller 500 may cause the light transmitter 510 to transmit a pulse of light as described above. The controller 500, further, may communicate with the timer 505 to receive a first time value representing a time at which the pulse of light was transmitted. The light may be directed through a connector 40 as illustrated, for example, in FIG. 1, conveyed through a conduit 35 (FIG. 2), passed to an electromagnetic energy (e.g., laser) handpiece 20, reflected from a first mirror 425 (FIG. 8), and directed to tip waveguides 430 (FIG. 8) that direct the light to a target surface, such as a surface of a tooth. Reflected or scattered light 435 (FIG. 8), which may be caused by fluorescence of caries on the tooth, may be directed through tip waveguides 430 and onto first mirror 425, reflected from the first mirror 425 and conveyed to the laser base unit 30 (FIG. 1) through the electromagnetic energy handpiece 20, the conduit 35, and the connector 40, and received by a light receiver 515 (FIG. 15).

According to one embodiment, the light receiver 515 directs the light to the splitter 520 that directs a portion of the light to a first filter 525 and that, further, directs another portion of the light to a second filter 530. As described above, the first filter 525 may comprise, for example, a narrow band filter that passes radiation at wavelengths of about 636 nm (i.e., substantially visible red light). The second filter 530 may comprise a second narrow band filter that passes radiation have wavelengths near 550 nm (i.e., substantially visible green light). Light from the first filter 525 (e.g., red light) may be received by the first photo detector 535, which creates a first electrical signal according to an intensity level of the light passed by the first filter 525. Similarly, light from the second filter 530 (e.g., green light) may be received by the second photo detector 540, which creates a second electrical signal according to an intensity level of the light passed by the second filter 530. The controller 500 may receive the first and second electrical signals and may compute a quotient as already described by, for example, dividing a magnitude of the first electrical sign a by a magnitude of the second electrical signal. The controller 500 may compare a result of the division with a stored threshold, and may provide an indication on the display device 550 according to the result.

The controller 500, further, may communicate with the timer 505 when first and second electrical signals are detected in order to determine a time delay between transmission of the light pulse and reception of a corresponding response. The controller 500 then may provide an indication to the display device 550 according to the time delay. Additionally, the controller 550 may determine a relative time delay as described below with reference to FIG. 14.

According to certain implementations, the output from a power or treatment fiber can be directed, for example, into fluid (e.g., an air and/or water spray or an atomized distribution of fluid particles from a water connection and/or a spray connection near an output end of the handpiece) that is emitted from a fluid output of the handpiece above a target surface (e.g., one or more of tooth, bone, cartilage and soft tissue). The fluid output may comprise a plurality of fluid outputs, concentrically arranged around a power fiber, as described in, for example, U.S. application Ser. No. 11/042, 824 and U.S. Provisional Application No. 60/601,415. The power or treatment fiber may be coupled to an electromagnetic energy source comprising one or more of a wavelength within a range from about 2.69 to about 2.80 microns and a wavelength of about 2.94 microns. In certain implementations the power fiber may be coupled to one or more of an Er:YAG laser, an Er:YSGG laser, an Er, Cr:YSGG laser and a CTE:YAG laser, and in particular instances may be coupled to one of an Er, Cr:YSGG solid state laser having a wavelength of about 2.789 microns and an Er:YAG solid state laser having a wavelength of about 2.940 microns. An apparatus including corresponding structure for directing electromagnetic energy into an atomized distribution of fluid particles above a target surface is disclosed in the below-referenced U.S. Pat. No. 5,574,247, which describes the impartation of laser energy into fluid particles to thereby apply disruptive forces to the target surface.

By way of the disclosure herein, a handpiece has been described that utilizes electromagnetic energy to diagnose and/or affect a target surface. In the case of procedures using optical energy, such as caries detection, the handpiece can include one or more power or treatment fibers for transmitting treatment energy to a target surface for treating (e.g., ablating) a dental structure, such as a tooth, a plurality of fibers for transmitting light (e.g., blue and/or white light) for illumination and/or diagnostics of a target such as a tooth (e.g., and optionally for other procedures such as curing or whitening), and a plurality of fibers for transmitting light from the target surface back to a sensor for analysis. In certain embodiments, the fibers that transmit blue light may also transmit white light. In accordance with one aspect of the invention herein disclosed, a handpiece comprises an illumination tube having a feedback signal end and a double mirror handpiece. In any of the embodiments described herein, the light for illumination and/or diagnostics may be transmitted simultaneously with, or intermittently with or separate from, transmission of the treatment energy and/or of the fluid from the fluid output or outputs.

In certain embodiments, the methods and apparatuses of the above embodiments can be configured and implemented for use (e.g., simultaneously or intermittently), to the extent compatible and/or not mutually exclusive, with existing technologies including any of the above-referenced apparatuses and methods. Corresponding or related structure and methods described in the following patents assigned to BioLase Technology, Inc., are incorporated herein by reference in their entireties, wherein such incorporation includes corresponding or related structure (and modifications thereof) in the following patents which may be (i) operable with, (ii) modified by one skilled in the art to be operable with, and/or (iii) implemented/used with or in combination with any part(s) of, the present invention according to this disclosure, that/those of the patents, and the knowledge and judgment of one skilled in the art: U.S. Pat. Nos. 5,741,247; 5,785,521; 5,968,037; 6,086,367; 6,231,567; 6,254,597; 6,288,499; 6,350,123; 6,389,193; 6,544,256; 6,561,803; 6,567,582; 6,610,053; 6,616,447; 6,616,451; and 6,744,790.

In view of the foregoing, it will be understood by those skilled in the art that the methods and apparatus of the present invention can facilitate detection of dental caries using laser devices. While this invention has been described with respect to various specific examples and embodiments, it is to be understood that the invention is not limited thereto and that it can be variously practiced. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention should not be limited by the disclosed embodiments, but is to be defined by reference to the appended claims.

What is claimed is:

1. A method of detecting dental caries, comprising:
   directing at least one excitation pulse of laser energy toward a surface of a tooth;
   receiving at least one corresponding return pulse of fluorescent radiation responsive to the electromagnetic energy; and
   determining at least one time delay between the at least one excitation pulse and the at least one corresponding returned pulse.

2. The method as set forth in claim 1, further comprising determining a relative time delay according to the at least one time delay.

3. The method as set forth in claim 2, wherein the determining of a relative time delay comprises:
   maintaining a running average of time delays between excitation pulses and corresponding returned pulses;
   receiving a time delay; and
   comparing the time delay with the running average.

4. The method as set forth in claim 1, further comprising comparing a returned pulse with a corresponding excitation pulse according to at least one of intensity, time delay, and spectral distribution.

5. The method as set forth in claim 1, comprising receiving an indication of a depth of carries according to the time delay.

6. The method as set forth in claim 1, further comprising directing electromagnetic energy toward caries to perform caries therapy.

7. An apparatus for detecting dental caries, comprising:
   an electromagnetic energy device capable of generating at least one excitation pulse of electromagnetic energy;
   a delivery system capable of directing the at least one excitation pulse toward a surface of a tooth;
   a detector capable of receiving at least one return pulse of fluorescent radiation corresponding to the at least one excitation pulse, the detector comprising an electromagnetic radiation receiver, a splitter, at least one filter which comprises a first narrow band filter and at least one photo detector; and
   a controller capable of measuring a time delay between the transmitting of the at least one excitation pulse and the receiving of the at least one return pulse.

8. The apparatus as set forth in claim 7, wherein the first narrow band filter passes electromagnetic radiation having wavelengths of about 636 nm.

9. The apparatus as set forth in claim 7, wherein the at least one filter further comprises a second narrow band filter.

10. The apparatus as set forth in claim 9, wherein the second narrow band filter passes electromagnetic radiation having wavelengths of about 550 nm.

11. The apparatus as set forth in claim 10, wherein:
   the at least one photo detector comprises a first photo detector and a second photo detector;

the first photo detector is capable of generating a first electrical signal according to electromagnetic radiation received from the first narrow band filter;

the second photo detector is capable of generating a second electrical signal according to electromagnetic radiation received from the second narrow band filter;

the controller is capable of determining a quotient by dividing a magnitude of the first electrical signal by a magnitude of the second electrical signal; and the controller is capable of comparing the quotient with a stored threshold and of providing an indication on a display device according to the result of the comparison.

12. An apparatus capable of detecting dental caries, comprising:

an electromagnetic energy device capable of generating a pulse of electromagnetic energy and directing the electromagnetic energy to a surface of a tooth;

a detector capable of receiving returned electromagnetic radiation from the tooth according to the electromagnetic energy; and a controller capable of measuring a time delay according to the electromagnetic energy and the returned electromagnetic radiation, the controller being capable of controlling a timer according to a time of generating the pulse of electromagnetic energy and a time of receiving a pulse of returned electromagnetic radiation.

13. The apparatus as set forth in claim 12, wherein the controller is capable of determining a running average of time delays, receiving a time delay, and comparing the time delay with the running average.

14. The apparatus as set forth in claim 13, further comprising:

an electromagnetic radiation receiver;

a splitter;

a first narrow band filter;

a second narrow band filter;

a first photo detector; and a second photo detector.

15. The apparatus as set forth in claim 14, wherein:

the first narrow band filter passes electromagnetic radiation having wavelengths of about 636 nm;

the second narrow band filter passes electromagnetic radiation having wavelengths of about 550 nm;

the first photo detector is capable of generating a first electrical signal according to an intensity of electromagnetic radiation received from the first narrow band filter; and the second photo detector is capable of generating a second electrical signal according to an intensity of electromagnetic radiation received from the second narrow band filter.

16. The apparatus as set forth in claim 15, further comprising a controller configured to receive the first electrical signal and the second electrical signal, and to determine a quotient by dividing a magnitude of the second electrical signal by a magnitude of the first electrical signal.

* * * * *